(12) United States Patent
Wood et al.

(10) Patent No.: US 9,414,857 B2
(45) Date of Patent: Aug. 16, 2016

(54) DELIVERY SYSTEM ASSEMBLIES FOR IMPLANTABLE MEDICAL DEVICES

(71) Applicant: Medtronic, Inc., Minneapolis, MN (US)

(72) Inventors: Ronan Wood, Co. na Gaillimhe (IE); Todd J Sheldon, North Oaks, MN (US); Matthew D Bonner, Plymouth, MN (US); Sean Ward, Dublin (IE); Paula McDonnell, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 42 days.

(21) Appl. No.: 14/548,958

(22) Filed: Nov. 20, 2014

(65) Prior Publication Data
US 2016/0143661 A1    May 26, 2016

(51) Int. Cl.
| | | |
|---|---|---|
| *A61B 19/00* | (2006.01) | |
| *A61B 17/34* | (2006.01) | |
| *A61N 1/362* | (2006.01) | |
| *A61N 1/372* | (2006.01) | |
| *A61B 17/00* | (2006.01) | |

(52) U.S. Cl.
CPC ....... *A61B 17/3468* (2013.01); *A61B 17/00234* (2013.01); *A61N 1/362* (2013.01); *A61N 1/37205* (2013.01); *A61B 2017/00022* (2013.01); *A61B 2017/00323* (2013.01)

(58) Field of Classification Search
CPC ............ A61N 1/37205; A61N 1/0587; A61N 2001/0578; A61B 17/3468; A61B 2017/00243; A61M 25/0026; A61M 25/0105
USPC ............................. 606/129; 607/119; 604/528
See application file for complete search history.

(56) References Cited

U.S. PATENT DOCUMENTS

| | | | |
|---|---|---|---|
| 5,184,625 A | 2/1993 | Cottone, Jr. et al. | |
| 5,836,960 A | 11/1998 | Kolesa et al. | |
| 6,716,238 B2 | 4/2004 | Elliott | |
| 6,987,995 B2 * | 1/2006 | Drysen ............ | A61M 25/0136 600/374 |
| 2010/0094314 A1 | 4/2010 | Hernlund et al. | |
| 2010/0274227 A1 | 10/2010 | Khairkhahan et al. | |
| 2012/0197373 A1 | 8/2012 | Khairkhahan et al. | |
| 2013/0035748 A1 | 2/2013 | Bonner et al. | |
| 2013/0079798 A1 | 3/2013 | Tran et al. | |

(Continued)

OTHER PUBLICATIONS (PCT/US2015/060510) PCT Notification of Transmittal of the International Search Report and the Written Opinion of the International Searching Authority, mailed Feb. 22, 2016, 11 pages.

(Continued)

*Primary Examiner* — Katherine M Shi
(74) *Attorney, Agent, or Firm* — Evans M. Mburu

(57) ABSTRACT

An inner member of an improved assembly for a delivery system includes a first segment formed by a multi-lumen tubing surrounded by a braided tubing, and a second segment formed by a single-lumen tubing that extends within a distal portion of the braided tubing. The single-lumen tubing accommodates an antenna of a medical device, is in fluid communication with three lumens of the multi-lumen tubing, and opens into a flared distal end of the inner member. A distal-most portion of an outer tube of the system contains the flared distal end and an enclosure of the medical device abutting the distal end. A pull wire of the assembly extends within another lumen of the multi-lumen tubing and between the single-lumen tubing and the distal extent of the braided tubing, and is coupled to a pull band mounted in a cone member that forms the flared distal end.

5 Claims, 8 Drawing Sheets

(56) References Cited

U.S. PATENT DOCUMENTS

| | | |
|---|---|---|
| 2013/0103047 A1 | 4/2013 | Steingisser et al. |
| 2013/0131591 A1* | 5/2013 | Berthiaume ......... A61N 1/3756 604/95.04 |
| 2013/0131693 A1 | 5/2013 | Berthiaume et al. |
| 2015/0094668 A1* | 4/2015 | Wood ................ A61M 25/0105 604/256 |

OTHER PUBLICATIONS

Wood et al., "Interventional Medical Systems, Tools, and Assemblies", U.S. Appl. No. 14/039,937, filed Sep. 27, 2013, 32 pages.

Sheldon et al., "Leadless Pacing System Including Sensing Extension", U.S. Appl. No. 62/025,690, filed Jul. 17, 2014, 30 pages.

* cited by examiner

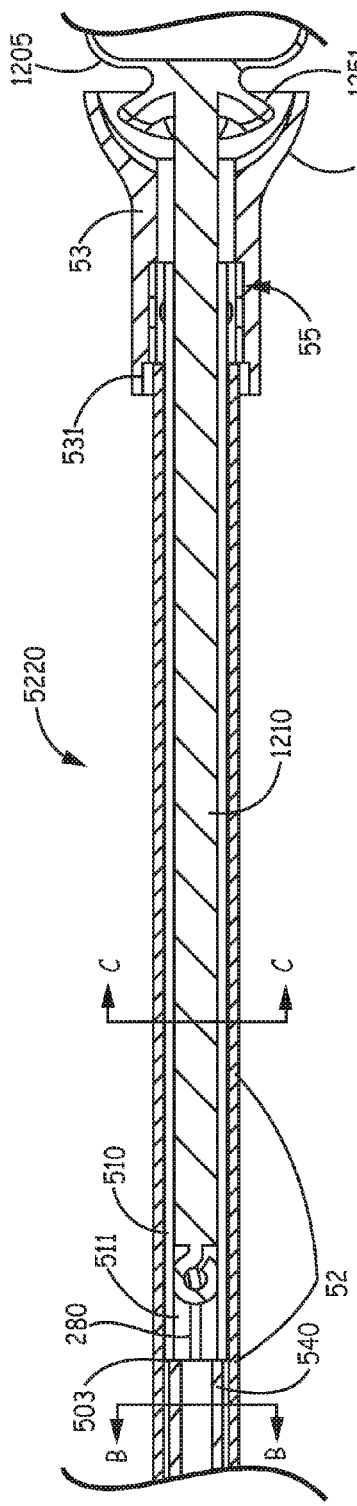
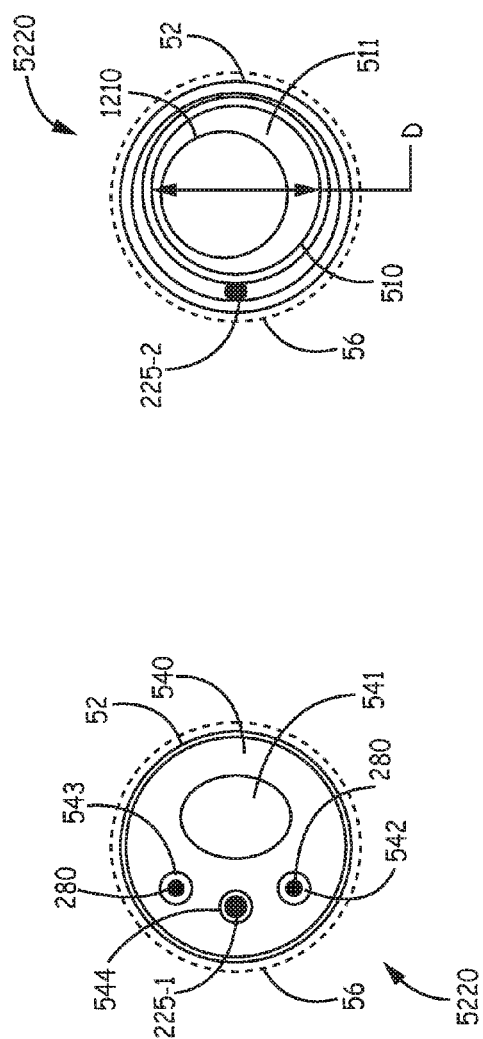
FIG. 5A
FIG. 5B
FIG. 5C

DELIVERY SYSTEM ASSEMBLIES FOR IMPLANTABLE MEDICAL DEVICES

TECHNICAL FIELD

The present invention pertains to the delivery of implantable medical devices, and more particularly to improved assemblies for systems that facilitate percutaneous transvenous deployment of relatively compact implantable cardiac medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues sometimes associated with elongate lead wires are well known to those skilled in the art and have motivated the development of cardiac pacing devices that are wholly contained within a relatively compact package for implant in close proximity to the pacing site, for example, within a right ventricle RV of the heart. With reference to FIG. 1, such a device 100 is shown, having been deployed by an exemplary delivery system 200 at an implant site in the right ventricular apex.

FIG. 1 illustrates device 100 including a hermetically sealed enclosure 105 containing pulse generator electronics and a power source (not shown), pace/sense electrodes 111, 112 formed on an exterior surface of enclosure 105, and a fixation member 115, which is mounted to a distal end of enclosure 105, in proximity to electrode 111, in order to fix, or secure electrode 111 against the endocardial surface at the implant site. Enclosure 105 is preferably formed from a biocompatible and biostable metal such as titanium overlaid with an insulative layer, for example, medical grade polyurethane or silicone, except where electrode 112 is formed as an exposed portion of the metal. A hermetic feedthrough assembly, such as any suitable type known to those skilled in the art, couples electrode 111 to the pulse generator contained within device enclosure 105. FIG. 1 further illustrates a proximal end 121 of device enclosure 105 configured for temporary attachment of a tether 280, or some other type of retention member, that may be employed to test the engagement of fixation member 115 with tissue at the implant site, and/or to retain a temporary connection between the deployed medical device 100 and delivery system 200, if repositioning of device 100 is necessary.

FIG. 2A is a plan view of exemplary delivery system 200; and FIGS. 2B-C are plan views of exemplary outer and inner assemblies, respectively, of system 200. FIG. 2A illustrates system 200 including a handle 210 from which the elongate outer assembly of FIG. 2B extends. FIGS. 2A-B illustrate the outer assembly including an elongate outer tube 230, which has a proximal end 231 coupled to a first control member 211 of handle 210, and a stability sheath 250, which surrounds a limited length L of outer tube 230 and is fixed to handle 210. FIG. 2C illustrates the exemplary inner assembly, which extends within a lumen formed by outer tube 230 of the outer assembly in system 200; the inner assembly includes an elongate inner member 220, wherein inner member 220 includes a proximal end 221, which is fixed within handle 210, and a flared distal end 222, which is configured to conform to proximal end 121 of device 100. With reference to FIG. 2A, proximal end 221 of inner member 220 may be coupled to a stop cock 260 by a luer fitting (not shown), and distal end 222 of inner member 220 is contained in a distal-most portion 232 of outer tube 230, just proximal to a distal opening 203 thereof. With reference to FIG. 2D, which is a plan view of the distal end of system 200 having a cut-away section of outer tube 230, distal-most portion 232 is sized to contain device 100 therein, when proximal end 121 of device 100 abuts flared distal end 222 of inner member 220. FIG. 2C further illustrates the inner assembly including a pull wire 225, which is coupled to a second control member 212 of handle 210, at a proximal end 51 thereof, and which is anchored at a location 52, in proximity to distal end 222 of inner member 220, so that inner member 220 may be deflected, per arrow D (FIG. 2D), via movement of second control member 212, per arrow B (FIG. 2A). The deflection per arrow D translates to outer tube 230 of delivery system 200 and helps to orient distal-most portion 232 thereof so an operator may maneuver system 200 within a patient's venous system for deployment of device 100 to a target implant site like that shown in FIG. 1. With reference to FIG. 2E, once distal-most portion 232 is positioned in proximity to the target implant site, the operator may withdraw outer tube 230 relative to inner member 220 and device 100, per arrow W, via movement of first control member 211 per arrow A (FIG. 2A), in order to engage fixation members 115 of device 100 with tissue at the site.

Methods of use and construction details for exemplary delivery system 200 are described in a commonly assigned United States Patent Application, which has the Pre-grant Publication Number 2013/0079798 (Ser. No. 13/239,990). Furthermore, an alternative exemplary delivery system, similar to a delivery system 300 shown in the plan view of FIG. 3, is described in another commonly assigned United States Patent Application, which has the Ser. No. 14/039,937. In contrast to system 200, outer tube 230 of system 300 is shown including a pre-formed bend 236, and a handle 310 of system 300, as described in the '937 application, contains a stop cock within a sidewall thereof, and further includes a flushing assembly 315. System 300 may be employed to deploy medical device 100 in a similar fashion to that described for system 200. Although delivery systems like systems 200 and 300 have been disclosed and are known in the art, there is still a need for improved assemblies thereof, for example, which accommodate new and improved forms of cardiac pacing devices that are wholly contained within a relatively compact package for implant in close proximity to the pacing site, for example, like medical device 1200, which is described below in conjunction with FIGS. 4A-B.

SUMMARY

An improved assembly for a delivery system, according to some embodiments of the present invention, extends within an elongate outer tube of the system and includes an elongate inner member. The inner member includes a first segment, formed by a multi-lumen tubing, and a braided tubing that surrounds the multi-lumen tubing and extends distally from a distal end thereof, and a second segment, formed by a single-lumen tubing extending within the distal extent of the braided tubing and defining a lumen that opens into a flared distal end of the inner member. The lumen is sized to accommodate an antenna of a medical device and is in fluid communication with three lumens of the plurality of lumens defined by the multi-lumen tubing. The flared distal end, formed by a cone member of the assembly, is preferably configured to conform to a proximal end of a hermetic enclosure of the medical device, from which the antenna extends proximally, and a distal-most portion of the elongate outer tube of the system is configured to contain the flared distal end together with the medical device enclosure abutting the flared distal end. The inner assembly further includes a pull wire that has a proximal end coupled to a control member of a handle of the system, and a distal end coupled to a pull band mounted in the cone member. A first length of the pull wire extends distally from the proximal end thereof, within another lumen of the plurality of lumens defined by the multi-lumen tubing of the first segment of the inner member, and a second length of the pull wire extends from the first length to the distal end thereof, between the single-lumen tubing of the second segment of the inner member and the distal extent of the braided tubing of the first segment of the inner member.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIG. 5A is a longitudinal cross-section of a portion of an improved inner assembly for a delivery system like either of those shown in FIGS. 2A and 3, according to some embodiments;

FIGS. 5B-C are cross-sections according to section lines B-B and C-C, respectively, of FIG. 5A, according to some embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
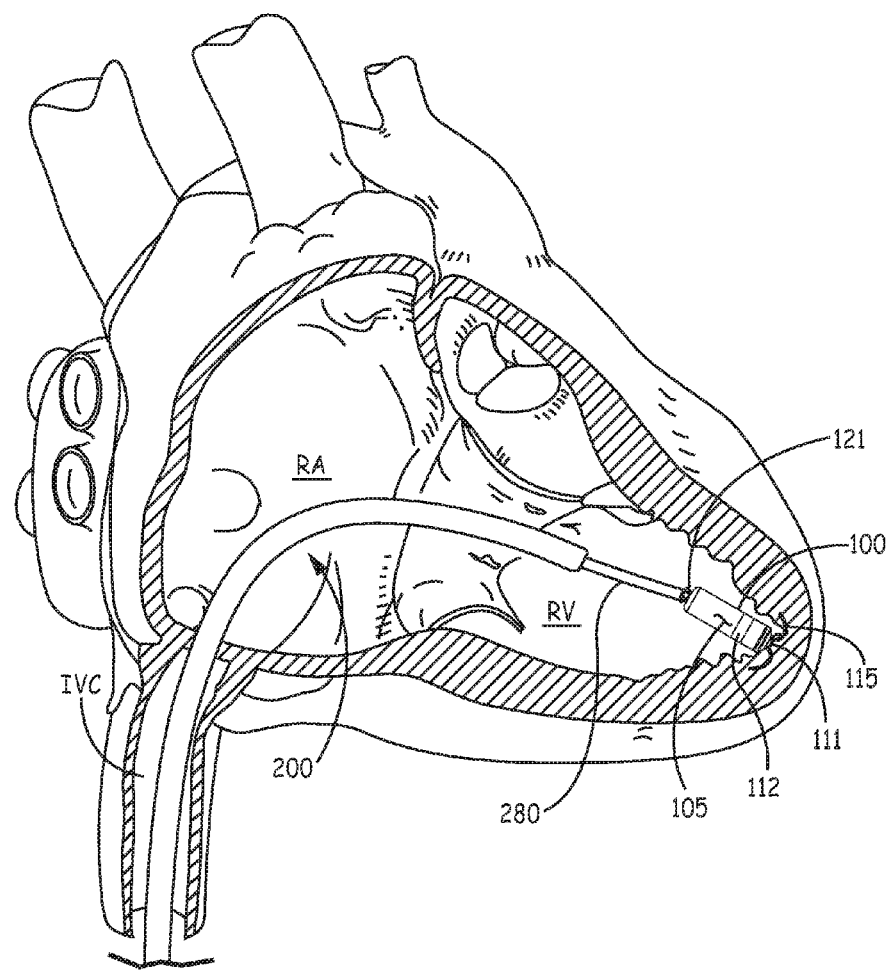
FIG. 1 is a schematic showing an example of an implanted cardiac stimulation device.
Figure 2A:
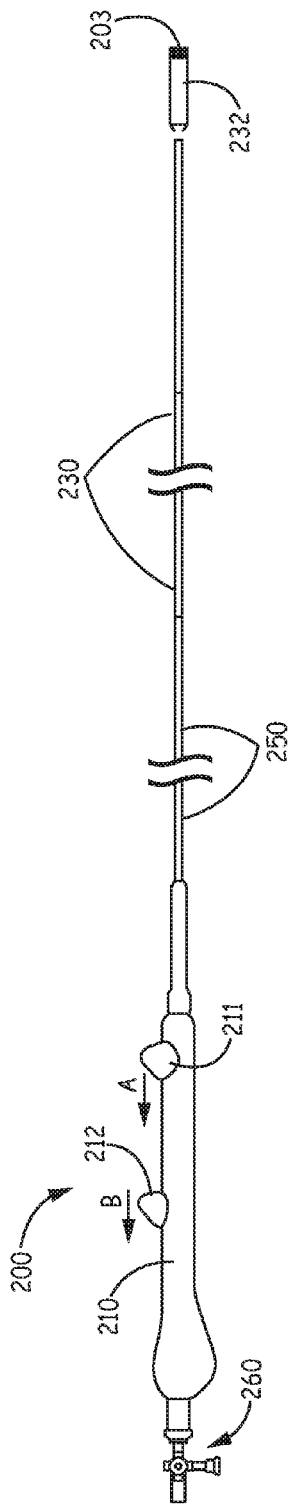
FIG. 2A is a plan view of an exemplary delivery system.
Figure 2B:
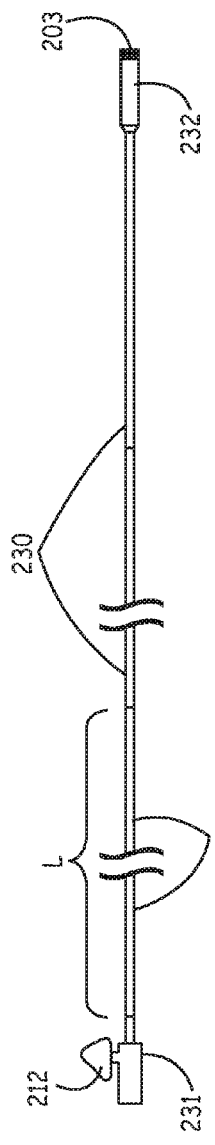
FIGS. 2B-C are plan views of inner and outer subassemblies, respectively, of the exemplary system shown in FIG. 2A.
Figure 2C:
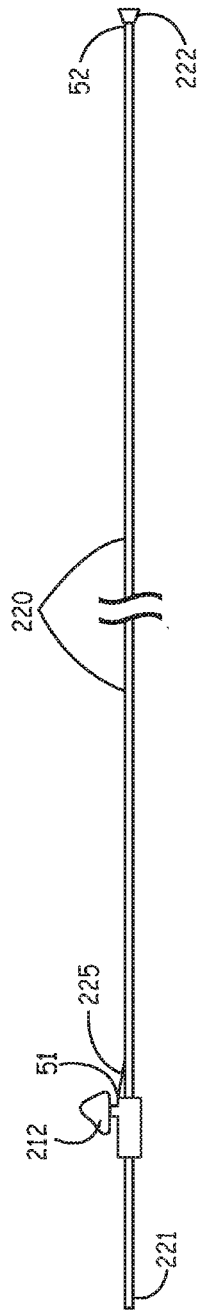
Figure 2D:
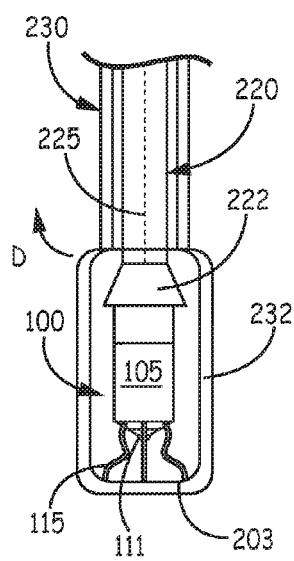
FIGS. 2D-E are plan views of the distal end of the exemplary system shown in FIG. 2A.
Figure 2E:
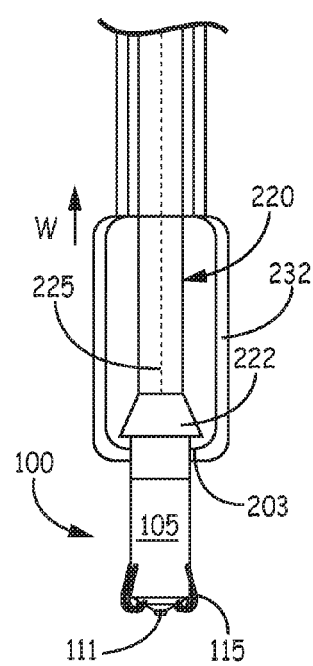
Figure 4A:
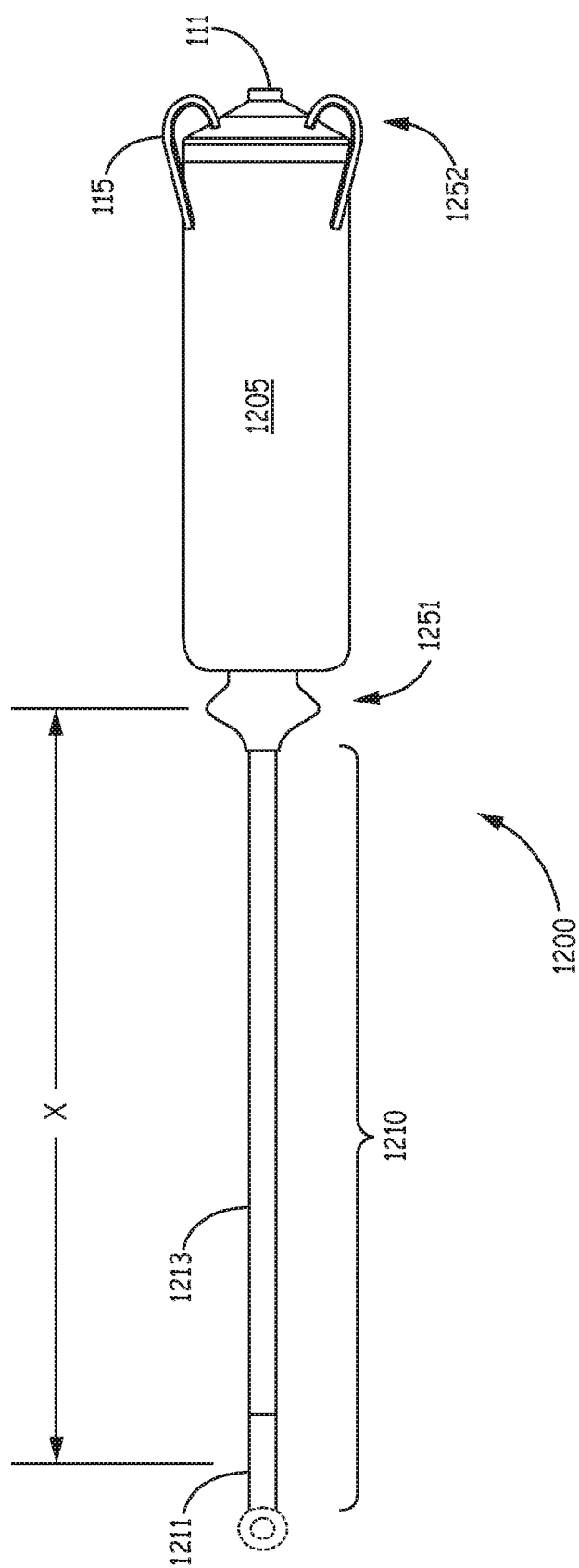
FIG. 4A is a plan view of another exemplary cardiac stimulation device.
Figure 4B:
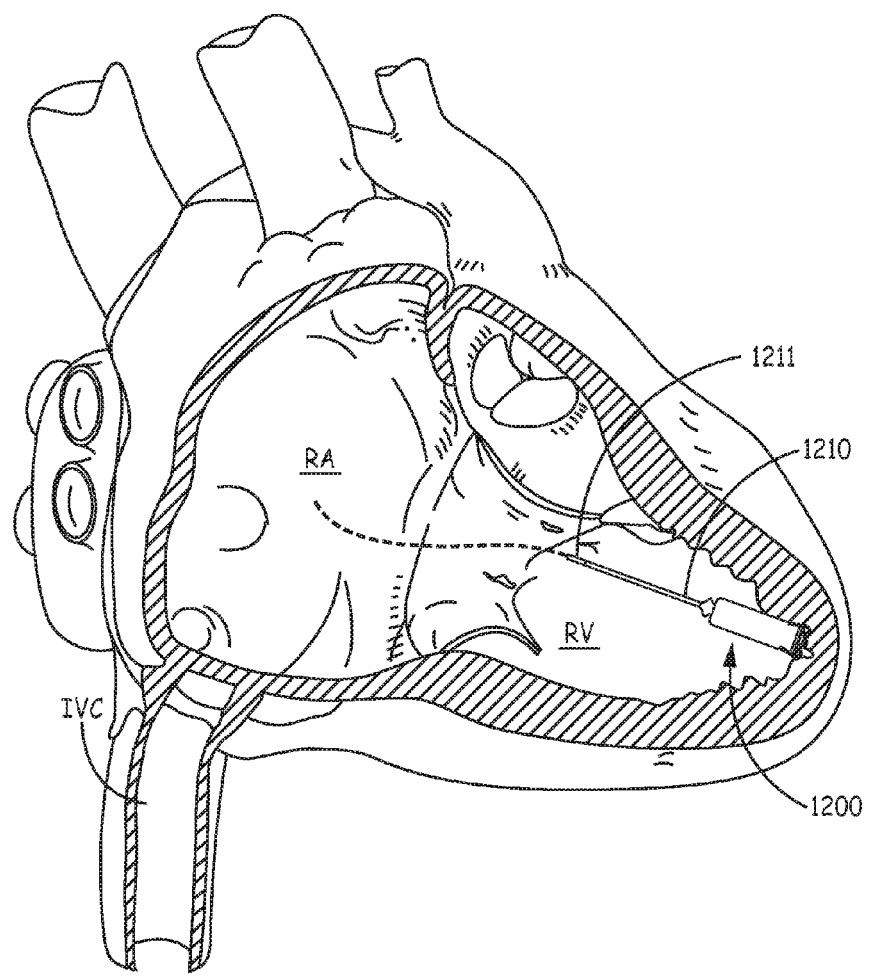
FIG. 4B is a schematic showing the device of FIG. 4A implanted.

FIG. 4A is a plan view of another exemplary cardiac stimulation device 1200 whose configuration has prompted the development of improved delivery system assemblies, according to embodiments described herein. FIG. 4A illustrates device 1200 including a hermetically sealed enclosure 1205, cardiac pacing and sensing electrodes 111, 1211, and fixation member 115 coupled to a distal end 1252 of device housing 1205. Like the above described enclosure 105 of device 100 (FIG. 1), enclosure 1205 of device 1200 contains pulse generator electronics and a power source within a relatively compact form factor, wherein electrode 111 is coupled to the controller via an hermetically sealed feedthrough assembly known in the art. Fixation member 115, like in device 100, holds electrode 111 in intimate contact with tissue at an implant site, for example, as illustrated in FIG. 4B. With further reference to FIG. 2A, unlike device 100, device 1200 includes an antenna 1210 on which sense electrode 1211 is mounted. Antenna 1210, for example, being formed by an insulated conductor 1213 that electrically couples electrode 1211 to the pulse generator electronics, extends proximally from a proximal end 1251 of device enclosure 1205, such that sense electrode 1211 is spaced a distance from proximal end 1251 of enclosure 1205, for example, to be located for atrial sensing (P-waves) when device 1200 is implanted in the right ventricle RV, for example, as shown in FIG. 4B. The distance may be between approximately 6 cm and approximately 10 cm, such that electrode 1211 is located in the right ventricle RV, as shown; or, according to alternate embodiments, the distance may be between approximately 10 cm and approximately 15 cm, such that electrode is located in the right atrium RA, for example, as indicated with the dashed line in FIG. 4B. A co-pending and commonly assigned U.S. Patent Application having the Ser. No. 62/025,690 provides a detailed description of an implantable medical device similar to device 1200, the description of which is hereby incorporated by reference.

Figure 3:
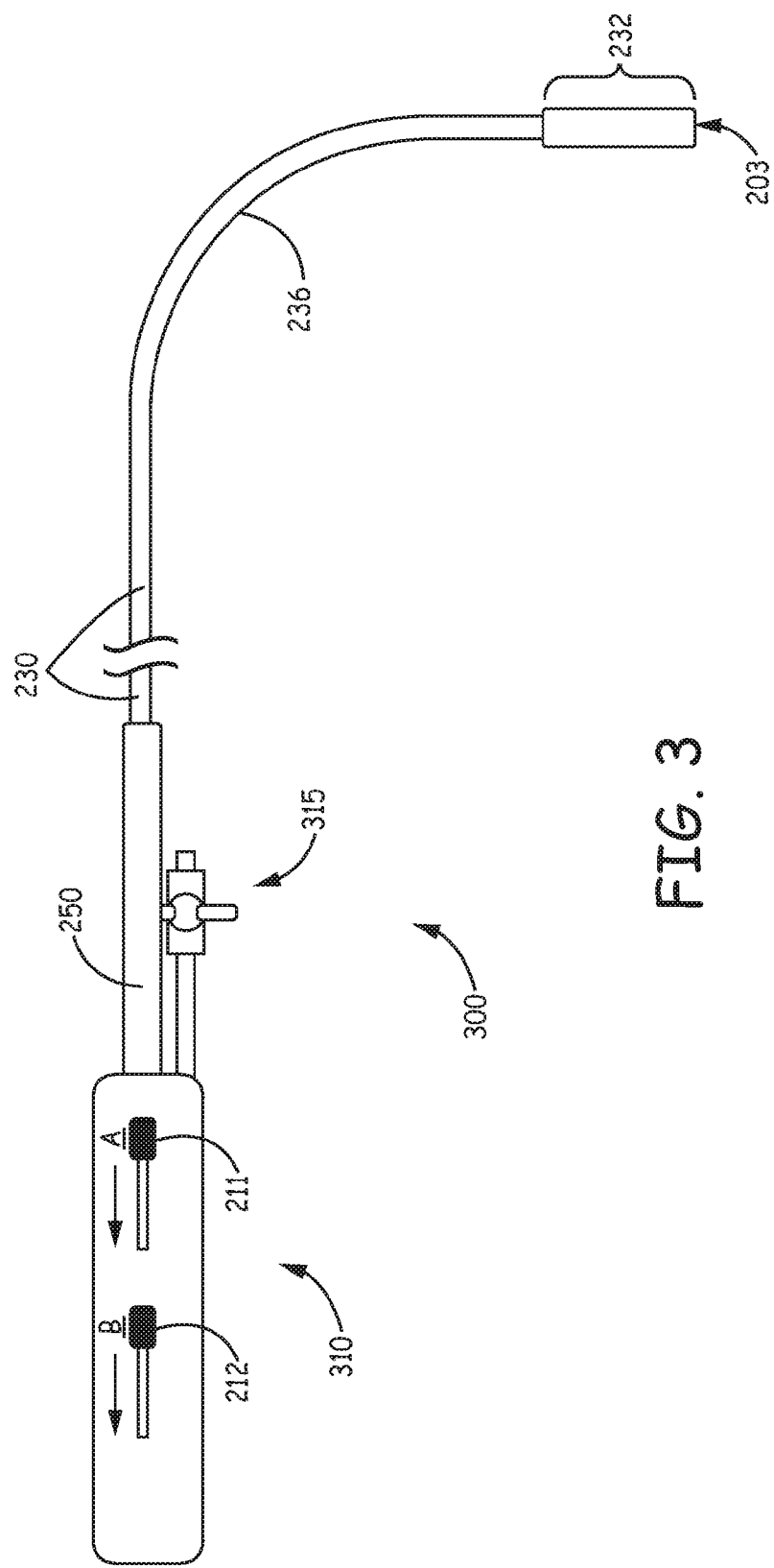
FIG. 3 is a plan view of another exemplary delivery system.

FIG. 5A is a longitudinal cross-section of a portion of an improved assembly 5220, according to some embodiments, for an inner member of a delivery system, for example, inner member 220 of either system that is described above in conjunction with FIGS. 2A-3; and FIGS. 5B-C are cross-section views through section lines B-B and C-C, respectively of FIG. 5A. FIGS. 5A-C illustrate assembly 5220 including a multi-lumen tubing 540 and a single-lumen tubing 510, wherein tubing 510 extends distally from a distal end 503 of multi-lumen tubing 540 to a cone member 53 of assembly 5220. Cone member 53 is shown forming flared distal end 222 of the above-described inner member 220, which conforms to a proximal end 1251 of device enclosure 1251; and a single lumen 511 formed by single-lumen tubing 510, which opens into flared distal end 222, is shown being sized to contain antenna 1210 of device 1200. According to an exemplary embodiment, a length of lumen 511 is between approximately 6 cm and approximately 16 cm, and a diameter D of lumen 511 is approximately 0.070 inch, minimum. With reference to FIGS. 5B-C, assembly 5220 further includes a braided tubing 52, which surrounds multi-lumen tubing 540 and single lumen tubing 510, and an optional sleeve 56 extending around braided tubing 52. A length of multi-lumen tubing 540 is preferably at least 100 cm, and, with reference back to FIGS. 2A-3, it should be understood that, when assembly 5220 forms inner member 220, multi-lumen tubing 540 extends proximally into handle 210.

Figure 6:
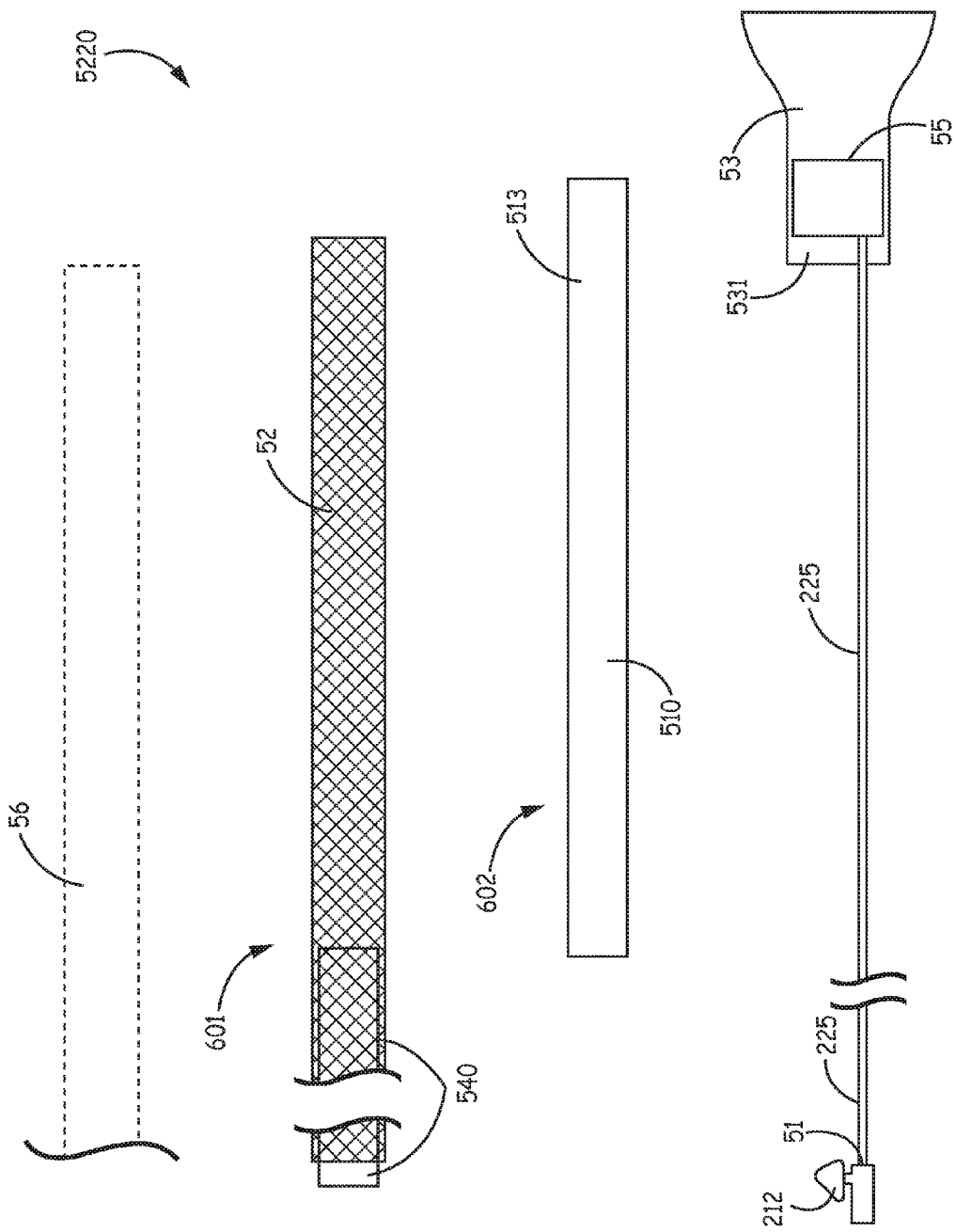
FIG. 6 is an exploded plan view of the portion of the improved inner assembly of FIG. 5A.

FIG. 6 is an exploded plan view of assembly 5220, wherein multi-lumen tubing 540 and braided tubing 52 are shown forming a first elongate segment 601 of the inner member, and wherein single-lumen tubing 510 is shown forming a second elongate segment 602 of the inner member. FIG. 6 illustrates braided tubing 52 surrounding multi-lumen tubing 540 and extending distally from distal end 503 thereof, wherein the distal extent of braided tubing 52 defines a lumen to receive single-lumen tubing 510 for the integration of second elongate segment 602 together with first elongate segment 601. Assembly 5220 may also include the aforementioned optional sleeve 56 configured to fit around braided tubing 52 for the reinforcement of a junction between multi-lumen tubing 540 and single-lumen tubing 510, when segments 601, 602 are integrated together. FIG. 6 further illustrates assembly 5220 including pull wire 225 (i.e. 0.010" stainless steel wire coated with PTFE) coupled to a pull band 55, which is mounted in cone member 53, wherein pull wire 225 extends proximally from the coupling to pull band 55 to the above described coupling between proximal end 51 of pull wire 225 and second control member 212 of handle 210, 310. The integration of pull wire 225 into assembly 5220 may be appreciated with reference back to FIGS. 5B-C.

FIGS. 5B-C illustrate multi-lumen tubing 540 defining first, second, third, and fourth elongate lumens 541, 542, 543, 544, wherein fourth lumen 544 provides a passageway for a first length 225-1 of pull wire 225. FIG. 5C illustrates a second length 225-2 of pull wire 225 being sandwiched between single-lumen tubing 510 and braided tubing 52. According to the illustrated embodiment, the remaining lumens 541-543 are in fluid communication with single lumen 511 of single-lumen tubing 510 and with one or more ports formed in handle 210, 310. FIG. 5B illustrates first lumen 541 being somewhat larger than lumens 542-544, for example, to accommodate a snare tool (not shown), and second and third lumens 542, 543 providing passageways for first and second lengths of tether 280, which is shown looped through an eyelet structure terminating a distal end of antenna 1210.

With further reference to FIGS. 5B-C and 6, according to an exemplary construction method, first length 225-1 of pull wire 225 is inserted into fourth lumen 544 of multi-lumen tubing 540, for example, before coupling proximal end 51 of pull wire 225 to control member 212 and after coupling second length 225-2 of pull wire 225 to pull band 55, so that second length 225-2 extends within the distal extent of braided tubing 52, sandwiched between braided tubing 52 and single-lumen tubing 510. Then first and second segments 601, 602 are integrated together, for example, by reflowing a wall of the distal extent of braided tubing 52, according to any suitable process known in the art, so that the wall of braided tubing 52 adheres to a wall of single-lumen tubing 510. The wall of braided tubing 52 may have been reflowed together with a wall of multi-lumen tubing 540 either before or after inserting first length 225-1 of pull wire 225 therein, and either before or during the reflow of the distal extent of the wall of braided tubing 52. FIG. 6 illustrates a distal end 513 of single-lumen tubing 510 that extends distally beyond braided tubing 52, when first and second segments 601, 602 are integrated together, and which extends within pull band 55 when pull wire 225 and pull band 55 are in position, having cone member 53 assembled thereover, as shown in FIGS. 5A and 6. A proximal end 531 of cone member 53 overlaps braided tubing 52 and single-lumen tubing 510 for attachment thereto, preferably by reflowing proximal end 531 to create a bond between cone member 53 and braided tubing 52 and single-lumen tubing 510. Optional sleeve 56, when included in assembly 5220, may be integrated together with segments 601, 602 during the aforementioned re-flow process, according to some construction methods.

According to an exemplary embodiment: single-lumen tubing 510 is formed from a medical grade fluoropolymer liner, for example, polytetrafluoroethylene (PTFE); braided tubing 52 is formed by a 304 stainless steel braid (0.001"× 0.005"; 65 pics per inch) set in a medical grade polymer, for example, a 63D durometer PEBAX®; optional sleeve 56 is formed from a medical grade polyether block amide, for example, a 35D durometer PEBAX®; multi-lumen tubing 540 is formed from a medical grade polymer, such as 55D durometer PEBAX®, preferably with a fluoropolymer lining each lumen 541-544, for example, PTFE; cone member 53, for example, an injection molded component, is formed from a medical grade polymer, such as 72D durometer PEBAX® loaded with 20% $BaSO_4$ (radiopacity for fluoroscopic visibility); and pull band 55 is formed from a medical grade stainless steel ring.

In the foregoing detailed description, the invention has been described with reference to specific embodiments. However, it may be appreciated that various modifications and changes can be made without departing from the scope of the invention as set forth in the appended claims.

The invention claimed is:

1. An improved assembly for a delivery system that facilitates deployment of an implantable medical device, the medical device including a pulse generator, an hermetic enclosure containing the pulse generator, and an antenna extending proximally from a proximal end of the enclosure and being electrically coupled to the pulse generator, and the system comprising: a handle including a first control member and a second control member; an elongate inner member including a proximal end fixed within the handle and a flared distal end spaced apart from the proximal end and being configured to conform to the proximal end of the hermetic enclosure of the medical device; a pull wire; and an elongate outer tube forming a lumen in which the inner member extends, the outer tube including a proximal end and a distal-most portion, the proximal end being coupled to the first control member of the handle, the distal-most portion being sized to contain the distal end of the inner member and the medical device enclosure, when the proximal end of the device enclosure abuts the distal end of the inner member, and the outer tube being movable, via the first control member, relative to the inner member and the contained device; and wherein the improved assembly comprises:
   a cone member forming the flared distal end of the inner member;
   a pull band mounted in the cone member;
   a multi-lumen tubing and a braided tubing forming a first elongate segment of the inner member, the multi-lumen tubing defining first, second, third, and fourth lumens, and the braided tubing surrounding the multi-lumen tubing and extending distally from a distal end of the multi-lumen tubing to the cone member;
   a single-lumen tubing forming a second segment of the inner member, the single-lumen tubing extending within the distal extent of the braided tubing of the first segment, the single-lumen tubing defining a single lumen sized to contain the antenna of the medical device, being in fluid communication with the first, second, and third lumens of the multi-lumen tubing, and opening into the flared distal end of the inner member; and
   the pull wire including a first length and a second length, the first length of the pull wire extending within the fourth lumen of the multi-lumen tubing of the first segment of the inner member, distally from a proximal end of the pull wire, the proximal end of the pull wire being coupled to the second control member of the handle, and the second length of the pull wire extending distally from the first length to a distal end of the pull wire, being sandwiched between the single-lumen tubing of the second segment of the inner member and the distal extent of the braided tubing of the first segment of the inner member, the distal end of the pull wire being coupled to the pull band.

2. The assembly of claim 1, further comprising a sleeve extending around the braided tubing of the first segment of the inner member and along lengths of the both the first segment and the second segment of the inner member.

3. The assembly of claim 1, wherein the cone member of the inner member includes a proximal end that overlaps the braided tubing of the first segment of the inner member and the single-lumen tubing of the second segment of the inner member proximal to the pull band.

4. The assembly of claim 1, wherein a length of the multi-lumen tubing of the first segment of the inner member is at least approximately 100 cm, and a length of the second segment of the inner member is between approximately 6 cm and approximately 16 cm.

5. The assembly of claim 1, wherein the single-lumen tubing of the second segment of the inner member comprises a fluoropolymer liner of the single lumen.

* * * * *